Dec. 5, 1967 H. B. LEWIS Plant Pat. 2,781
AZALEA PLANT
Filed Sept. 28, 1966
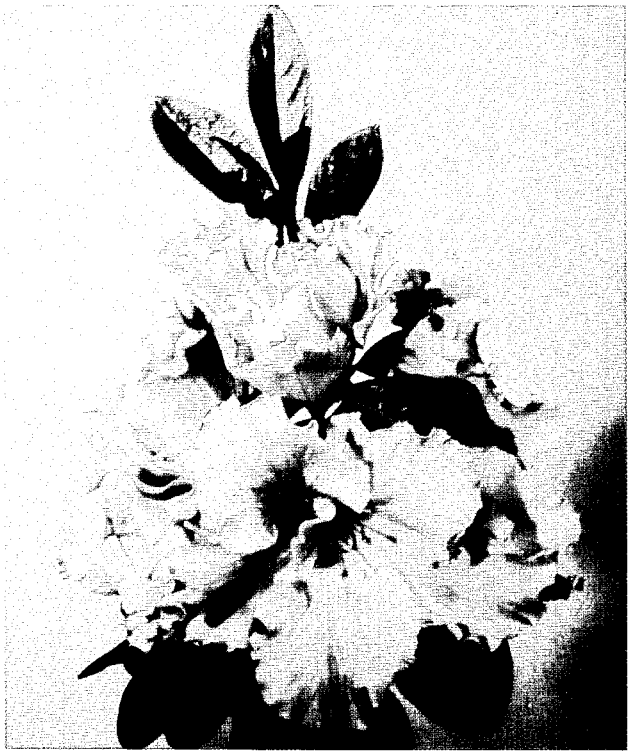
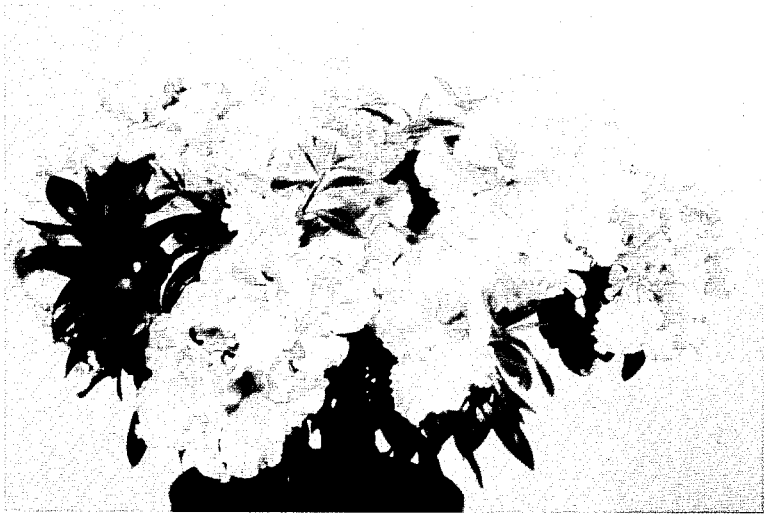
Inventor.
H. B. Lewis
By: Robb & Robb
Attorneys.

United States Patent Office

Plant Pat. 2,781
Patented Dec. 5, 1967

2,781
AZALEA PLANT

Hubert B. Lewis, 16562 E. Leffingwell Road,
Whittier, Calif. 90603

Filed Sept. 28, 1966, Ser. No. 582,769
1 Claim. (Cl. Plt.—56)

The present invention relates to a new and distinct variety of azalea plant which was discovered by me in my greenhouses at Whittier, Calif., as a sport of the azalea variety known as "Dr. Bergman" (unpatented).

At the time of my discovery aforementioned, I was growing plants of the variety "Dr. Bergman" for commercial purposes, and was forcing some of the plants in my greenhouses. In the course of these operations, my attention was attracted to one particular plant which appeared to be distinctly different from all the others. Upon closer observation of this particular plant, I found that it had sported, and accordingly, I took steps to carefully preserve the sport, keep it under continued observation, and later, I asexually reproduced the sport by cuttings taken therefrom, as performed in my greenhouses at Whittier, Calif. Further observations and tests of the progeny showed that they came true and that the distinctive characteristics of the sport were transmissible through succeeding propagations. This fully convinced me that the new sport represented a new and distinct variety, as evidenced by the following unique combination of characteristics which are outstanding therein and which distinguish the new variety from its parent, as well as from all other azalea varieties of which I am aware:

(1) A general similarity to the parent variety "Dr. Bergman" in respect to the color of its foliage and flowers, but having a larger foliage size;

(2) A much faster rate of growth than the parent variety aforesaid;

(3) Larger and more attractive flowers than those of the parent variety; and (4) A ruffled flower form.

The accompanying drawing shows a typical specimen plant of our new azalea variety, as well as typical specimens of the flowers and foliage on a somewhat enlarged scale, all as depicted in color as nearly true as it is reasonably possible to make the same in a color illustration of this character.

The following is a detailed description of my new variety, with color terminology in accordance with the Horticultural Colour Chart issued by Wilson Colour Ltd. in collaboration with the Royal Horticultural Society, except where general color terms of ordinary dictionary significance are obvious:

Locality where grown and observed: Whittier, Calif.

Propagation: Holds its distinguishing characteristics through succeeding propagations by cuttings.

*Plant*

Form: Bush; much-branched; compact.
Growth: Medium vigorous; compact.
Rooting: Medium.
Blooming habit: Good.
Blooming season: Usually in spring, but suitable for year around culture with normal treatment; good for forcing.

Foliage:
- *Size.*—Medium.
- *Quantity.*—Normal.
- *Color.*—New foliage: upper side—Spinach Green, Plate 0960/1, page 187; under side—Willow Green, Plate 000862/1, page 199. Old foliage: upper side—Parsley Green, Plate 00962, page 193; under side—Spinach Green, Plate 0960/3, page 187.
- *Shape.*—Oval pointed.
- *Texture.*—upper side—glossy. Under side—smooth.
- *Margin.*—Smooth edge.
- *Aspect.*—Good.
- *Disease resistance.*—Fairly comparable to that of other varieties, as determined by comparison with such other varieties grown under the same cultural conditions at Whittier, Calif.

*Flowers*

Borne: Two or three to stem.
Quantity of bloom: Free, both outdoors and in greenhouse.
Continuity: One season or intermittent, depending on culture.
Permanence: Lasting up to 3 weeks.
Petalage:
- *Number of petals under normal conditions.*—6 petals.
- *Color.*—Variegated from Carmine Rose, Plate 621/1, page 75, to white, with rest of petal Geranium Lake, Plate 20/2, page 20.
- *Texture.*—Fleshy; thick.
- *Appearance.*—Inside—single, with tufted center; very ruffled. Outside—very ruffled.
- *Shape.*—From single to semi-double.
- *Arrangement.*—Well arranged, with slightly overlapping petals.
- *Size of flower.*—From 3 inches to 3¾ inches in diameter.

Bud: Ruffled. Color—Chrysanthemum Crimson, Plate 824, page 169 at center, shading outward to Brick Red, Plate 016/2, page 106.

*Reproductive organs*

Stamens: Color—Geranium Lake, Plate 20/2, page 20.
Pollen: Color—yellow.
Styles: Color—Geranium Lake, Plate 20/1, page 20.
Ovaries: Color—green.

I claim:

A new and distinct variety of azalea plant, substantially as herein shown and described, characterized particularly as to novelty by the unique combination of a general similarity to the parent variety "Dr. Bergman" in resepct to the color of its foliage and flowers, but having a larger foliage size, a much faster rate of growth than the parent variety aforesaid, larger and more attractive flowers than those of the parent variety, and a ruffled flower form.

No references cited.

ROBERT E. BAGWILL, *Primary Examiner.*